United States Patent
Fujii et al.

(12) 
(10) Patent No.: US 6,267,983 B1
(45) Date of Patent: Jul. 31, 2001

(54) DERMATOLOGICAL PATCH AND PROCESS FOR PRODUCING THEREOF

(75) Inventors: Kimihiro Fujii; Kazuo Tanaka; Kazuya Ikawa, all of Kobe; Yasuhiro Ikeura; Shinji Yamasoto, both of Tosu, all of (JP)

(73) Assignees: Bando Chemical Industries, Ltd., Hyogo; Hisamitsu Pharmaceutical Co., Ltd., Saga, both of (JP)

( * ) Notice: Subject to any disclaimer, the term of this patent is extended or adjusted under 35 U.S.C. 154(b) by 0 days.

(21) Appl. No.: 09/319,577

(22) PCT Filed: Oct. 26, 1998

(86) PCT No.: PCT/JP98/04850

§ 371 Date: Aug. 11, 1999

§ 102(e) Date: Aug. 11, 1999

(87) PCT Pub. No.: WO99/21537

PCT Pub. Date: May 6, 1999

(30) Foreign Application Priority Data

Oct. 28, 1997 (JP) .................................................. 9-295103

(51) Int. Cl.$^7$ .............................. A61F 13/00; A61K 9/70; A61L 15/16

(52) U.S. Cl. .......................... 424/448; 424/443; 424/449

(58) Field of Search .................................. 424/443, 447, 424/448, 449

(56) References Cited

U.S. PATENT DOCUMENTS 3,971,753 * 7/1976 Frechtling et al. ............... 260/42.14

FOREIGN PATENT DOCUMENTS 4-057872A * 2/1992 (JP) .
6-287134 * 2/1992 (JP) .

* cited by examiner

Primary Examiner—Thurman K. Page
Assistant Examiner—S. Howard
(74) Attorney, Agent, or Firm—Merchant & Gould P.C.

(57) ABSTRACT

A transdermal patch which comprises: a substrate sheet comprises a composite film formed of a resin composition comprising 100 parts by weight of a polyvinyl chloride-polyurethane composite and 2–10 parts by weight of a styrene-ethylene-butylene-styrene copolymer, a first adhesive layer on the one side of the composite film, and a polyalkylene terephthalate film adhered to the one side of the composite film by means of the first adhesive layer, a primer layer which comprises a saturated polyester resin and is formed on the surface of the polyalkylene terephthalate film; and a second adhesive layer comprising a styrene-diene-styrene block copolymer containing a pharmaceutical agent layered on the primer layer.

A method for the manufacture of the above-mentioned substrate sheet comprises preparing the above resin composition molding the resin composition into a composite film by a calendar process, and then adhering a polyalkylene terephthalate film on one side of the composite film by means of an adhesive layer thereby forming the substrate sheet, and forming a primer layer comprising a saturated polyester resin on the outer surface of the polyalkylene terephthalate film.

15 Claims, 1 Drawing Sheet

DERMATOLOGICAL PATCH AND PROCESS FOR PRODUCING THEREOF

This application is a 371 of PCT/JP98/04850 Oct. 26, 1998.

TECHNICAL FIELD

The present invention relates to a transdermal or dermatological patch (i.e., the so-called a sticky plaster) where an adhesive layer containing a pharmaceutical agent is formed on a substrate, to a substrate sheet therefor, and to a method for the manufacture of the substrate sheet.

More particularly, the invention relates to a sticky transdermal patch in which transfer of the pharmaceutical agent to the substrate sheet does not occur, adhesion between the adhesive layer and the substrate is strong resulting in no so-called residual paste when applied to and then detached from skin, the constituting films in the substrate sheet consisting of layered film are strongly adhered each other, no stickiness on the surface is noted, and texture, smoothness and fitting to skin are all good and also relates to a substrate sheet therefor as well as to a method for manufacturing the substrate.

BACKGROUND OF THE INVENTION

A sticky transdermal patch in which an adhesive containing a pharmaceutical agent such as skin stimulating agent, anti-inflammatory agent, analgesic, etc. is layered on a substrate sheet has been widely used as a transcutaneous agent in the medical field already. In such a patch, it has been known, as described in JP-A-54-138124, that copolymer of a diene type, particularly, a block copolymer of a diene type is suitable as an adhesive because, when applied the patch for skin, it shows good adhesion and fitness to skin and an appropriate elasticity and, further, it does not irritate the skin upon removal but can be easily detached.

On the other hand, as a substrate sheet for the transdermal patch as mentioned above, a vinyl chloride resin which is soft and flexible fitting the skin is suitable. On the contrary, however, a sheet of the vinyl chloride resin has poor affinity for the block copolymer of a diene type as an adhesive and, particularly in the case of patch, the copolymer of a diene type as an adhesive contains higher fatty acids, liquid paraffin, and the like as plasticizers together with the pharmaceutical agents whereby its affinity for an adhesive is more inferior.

As a result, when an adhesive consisting of a block copolymer of a diene type is directly and just applied to the substrate sheet made of a vinyl chloride resin to prepare a patch, there is a disadvantage that an adhesion of the adhesive to the substrate sheet is inferior.

Moreover, when a transdermal patch has a substrate sheet formed of polyvinyl chloride resin and contains a pharmaceutical agent which has a strong property of diffusion and permeation, the pharmaceutical agent permeates and diffuses into the substrate sheet as well so that the substrate sheet is swollen and deteriorated. In some cases, the desired therapeutic effect is reduced. It is of course possible that an appropriate primer treatment is applied to the sheet of the vinyl chloride resin so that the affinity for the block copolymer of a diene type is improved. However, in that case, the plasticizer contained in the vinyl chloride resin sheet transfers to the adhesive layer so that the property of the adhesive is deteriorated.

Under such circumstances, the present inventors had already found that, when a soft vinyl resin film containing a plasticizer is adhered to a polyethylene terephthalate film to prepare a composite film and an adhesive layer comprising a block copolymer of a diene type containing a pharmaceutical agent is formed on the side of the polyethylene terephthalate film of the composite film, the olyethylene terephthalate functions as a barrier layer for the plasticizer and the pharmaceutical agent. Thus, there is neither transfer of the pharmaceutical agent to the substrate sheet nor transfer of the plasticizer to the adhesive layer.

However, even in such a transdermal patch, the plasticizer contained in the film of the vinyl chloride resin bleeds onto its surface resulting in stickiness of the surface. In addition, when the composite film is wound up in a roll, such a bleeding of the plasticizer onto the surface of the vinyl chloride resin film transfers to the polyethylene terephthalate film so that adhesion of the adhesive containing the pharmaceutical agent to the polyethylene terephthalate film becomes low.

In view of the above and for coping with the above-mentioned problems in the known transdermal patches, the present inventors proposed a transdermal patch in JP-A-5-65486 where polyethylene terephthalate film is adhered and layered to a film formed of a polyvinyl chloride-polyurethane composite (which may contain a polyester plasticizer) to prepare a substrate sheet and an adhesive layer comprising a styrene-diene-styrene block copolymer containing a pharmaceutical agent is formed on the side of the polyethylene terephthalate film of the substrate sheet.

In such a transdermal patch, the polyethylene terephthalate film functions as an effective barrier layer both to the plasticizer and the pharmaceutical agent. Accordingly, neither transfer of the pharmaceutical agent to the substrate sheet nor transfer of the plasticizer to the adhesive layer takes place. In addition, stickiness of the surface by bleeding of the plasticizer onto the film surface does not occur and, texture and fitting to skin are good as well.

However, when the composite film of polyvinyl chloride-polyurethane composite, which is a main constituent of the substrate sheet of the transdermal patch, is manufactured by a calendar process of the polyvinyl chloride-polyurethane composite, the composite has not good calendar processing property, but it forms such a film on the rolls which is often hardly removed from the rolls, whereupon not only the yield is poor but also the resulting film has poor gloss or luster whereby the commercial value is reduced.

Further, when the resulting polyvinyl chloride-polyurethane composite film is stored in a rolled state during the manufacturing steps for the transdermal patch of the invention, the so-called "blocking" where the film sticks each other occurs. Therefore, in the manufacture of a transdermal patch by pulling out (i.e., by rewinding) the polyvinyl chloride-polyurethane composite film from the roll followed by subjecting to various processes thereto, a lot of inconveniences are resulted whereby its smooth manufacture is disturbed.

As a further point, when a polyethylene terephthalate film is adhered to the polyvinyl chloride-polyurethane composite film to prepare a substrate sheet and an adhesive layer containing a pharmaceutical agent is formed on the surface of the substrate sheet to prepare a transdermal patch, adhesion between the polyvinyl chloride-polyurethane composite film and the polyethylene terephthalate film is not sufficient and various inconveniences are unavoidable. For example, when such a patch is applied to and then removed from the skin, the adhesive layer is detached from the polyvinyl chloride-polyurethane composite film together with the polyethylene terephthalate film remaining on the skin whereby the so-called "residual paste" (the first residual paste) is resulted. In addition, interlayer detachment may occur in the substrate sheet during storage whereby the commercial value of the product is significantly deteriorated.

Moreover, adhesion between the adhesive layer and the substrate sheet is weak. Thus, when such a patch is applied to and then removed from the skin, the "residual paste" (the second residual paste) may also take place.

In order to solve the latter one in the above-mentioned problems or in order to improve the adhesion between the adhesive layer and the substrate sheet, it is possible, as described in JP-A-6-35381, that various primers are applied onto the polyethylene terephthalate film so that the substrate and the adhesive are strongly adhered. However, some pharmaceutical agents may result in an undesirable interaction with the primers whereby the primer layer and the adhesive layer turn yellow or other color. That significantly lower the commercial value of the product as well.

The present invention has been completed for solving the above-mentioned various problems in the conventional transdermal patches. Accordingly, it is an object of the invention to provide a sticky transdermal patch in which a pharmaceutical agent does not transfer to the substrate sheet, adhesion of the adhesive with the substrate is strong, films which constitute the substrate sheet, that is, a layered film, strongly adhere each other, any of the above-mentioned first and second residual pastes does not occur when the product is applied to and then removed from the skin, stickiness on the surface is not noted, and texture, smoothness and fitting to skin are all excellent.

It is a further object of the invention to provide a substrate sheet for such a transdermal patch.

It is still an object of the invention to provide a method for manufacturing such a substrate sheet.

DISCLOSURE OF THE INVENTION

The transdermal patch in accordance with the present invention comprises: a substrate sheet which comprises a composite film formed of a resin composition comprising 100 parts by weight of a polyvinyl chloride-polyurethane composite and 2–10 parts by weight of a styrene-ethylene-butylene-styrene copolymer, a first adhesive layer on the one side of the composite film, and a polyalkylene terephthalate film adhered to said one side of the composite film by means of the first adhesive layer; a primer layer which comprises a saturated polyester resin and is formed on the surface of the polyalkylene terephthalate film; and a second adhesive layer comprising a styrene-diene-styrene block copolymer containing a pharmaceutical agent layered on the primer.

The substrate sheet for a transdermal patch in accordance with the invention comprises a composite film formed of a resin composition comprising 100 parts by weight of a polyvinyl chloride-polyurethane composite and 2–10 parts by weight of a styrene-ethylene-butylene-styrene copolymer, an adhesive layer on the one side of the composite film, and a polyalkylene terephthalate film adhered to said one side of the composite film by means of the adhesive layer.

The method for the manufacture of the substrate sheet for a transdermal patch in accordance with the invention comprises preparing a resin composition comprising 100 parts by weight of a polyvinyl chloride-polyurethane composite and 2–10 parts by weight of a styrene-ethylene-butylene-styrene copolymer, molding the resin composition into a composite film by means of a calendar process, and then adhering a polyalkylene terephthalate film on one side of the composite film by means of an adhesive layer.

DESCRIPTION OF PREFERRED EMBODIMENTS OF THE INVENTION

Figure 1:
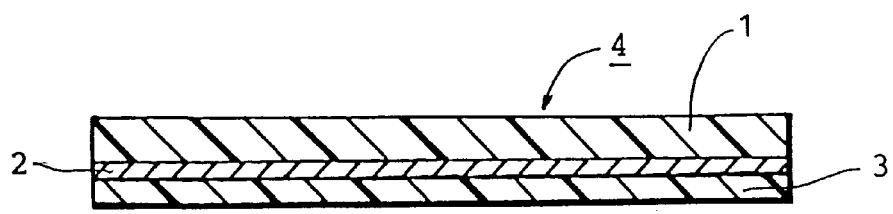
FIG. 1 is a cross section showing a basic example of the substrate sheet for the transdermal patch in accordance with the invention.

As shown in FIG. 1, the substrate sheet (4) for the transdermal patch in accordance with the present invention is basically formed by adhesion of a polyalkylene terephthalate film (3) by means of an adhesive layer (first adhesive layer) (2) to one side of a composite film (1) formed of a resin composition comprising a polyvinyl chloride-polyurethane composite and a styrene-ethylene-butylene-styrene copolymer.

Figure 2:
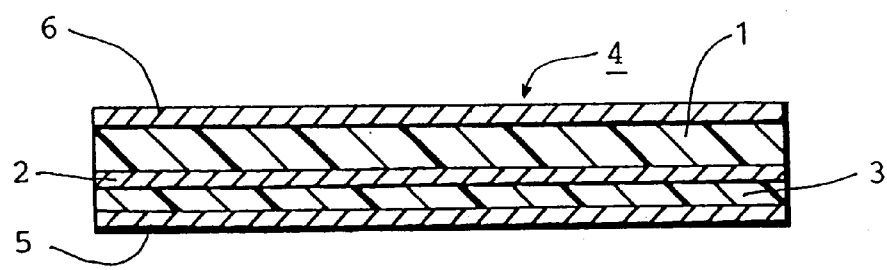
FIG. 2 is a cross section showing a preferred example of the substrate sheet for the transdermal patch in accordance with the invention.

According to a preferred embodiment of the invention, as shown in FIG. 2, the substrate sheet (4) of the invention comprises a composite film (1) having a polyalkylene terephthalate film (3) adhered to one side of the composite film (1) with an adhesive layer (2), and a primer layer (5) which comprises a saturated polyester resin and is formed on the outer surface of the polyalkylene terephthalate film, while a back treating layer (6) is formed on the other side of the composite film.

Figure 3:
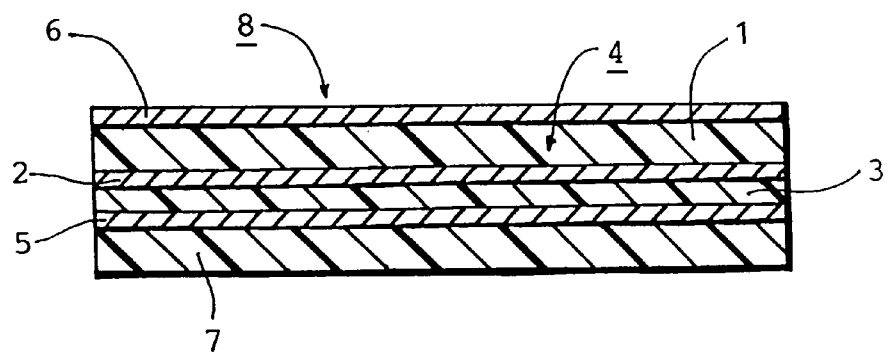
FIG. 3 is a cross section showing an example of the transdermal patch in accordance with the invention.

As shown in FIG. 3, the transdermal patch (8) in accordance with the invention comprises a substrate sheet (4) which comprises a composite film (4), a first adhesive layer (2) on one side of the composite film, and a polyalkylene terephthalate film (3) adhered to said one side of the composite film by means of the adhesive layer; a primer layer (5) which comprises a saturated polyester resin and is formed on the outer surface of the polyalkylene terephthalate film; and a second adhesive layer (7) comprising a styrene-diene-styrene block copolymer containing a pharmaceutical agent layered on the primer. A back treating layer (6) is formed on the other side of the composite film.

It is preferred that the transdermal patch of the invention is translucent having a light transmittance of about 20–50% so that its appearance upon application by sticking to the skin is good.

The substrate sheet of the invention is a layered film composed of a composite film formed of a resin composition comprising 100 parts by weight of a polyvinyl chloride-polyurethane composite and 2–10 parts by weight of a styrene-ethylene-butylene-styrene copolymer and a polyalkylene terephthalate film adhered by means of an adhesive to the composite film.

As described in JP-A-1-185312, the polyvinyl chloride-polyurethane composite may be prepared by impregnating powdery polyvinyl chloride with polyurethane-forming materials, followed by subjecting the resulting mixture to a polyurethane producing reaction.

The polyurethane-forming materials comprise a polyisocyanate and a polyol together with, if necessary, a catalyst. The polyvinyl chloride-polyurethane composite may be prepared as a powdery product by mixing the above-mentioned polyurethane-forming materials and either by impregnating a powdery polyvinyl chloride with the resulting liquid mixture of the polyurethane-forming materials (together with a catalyst if necessary) or by impregnating the powdery polyvinyl chloride with a polyol and then with a polyisocyanate (and a catalyst if necessary), followed by heating and cooling the resulting mixture upon completion of the reaction.

In the manufacture of such a polyvinyl chloride-polyurethane composite, the powdery polyvinyl chloride may be previously compounded, if necessary, with a stabilizer such as calcium-zinc stabilizer, calcium stearate, zinc stearate or tris(nonylphenyl) phosphite, as well as a lubricant, a coloring agent, and the like. Alternatively, a stabilizer, lubricant, coloring agent, etc. may be compounded if necessary after the manufacture of polyvinyl chloride-polyurethane composite.

In the manufacture of the polyvinyl chloride-polyurethane composite, a polyisocyanate is usually used in such an amount that the molar ratio of isocyanate group (NCO)/hydroxyl group (OH) is within a range of from 0.5 to 2.0 while a polyol is usually used in such an amount of 10–150 parts by weight or, preferably, 20–100 parts by weight to 100 parts by weight of polyvinyl chloride.

Accordingly, the polyvinyl chloride-polyurethane composite is a kind of mixture (a blend) of polyvinyl chloride with the polyurethane obtained by the reaction of the polyisocyanate with the polyol in the presence of polyvinyl chloride. The polyvinyl chloride-polyurethane composite prepared in this manner is then kneaded, made into pellets and molded into film by an extruder equipped with T die whereupon a polyvinyl chloride-polyurethane composite film is prepared.

It is preferred that the polyvinyl chloride-polyurethane composite has a Shore A hardness (23° C.) of within a range of 40–90 so that the sheet substrate resulted therefrom has both good flexibility and strength as a substrate sheet for the transdermal patch. Such a polyvinyl chloride-polyurethane composite is commercially available as, for example, "Dominas" from Tosoh K. K. In the present invention, such a commercially available product may be appropriately used.

According to the invention, the polyvinyl chloride-polyurethane composite prepared as such and the styrene-ethylene-butylene-styrene copolymer are then kneaded using rolls and the resulting resin composition is made into film by any means for use as a composite film for the manufacture of a substrate film. For example, the resin composition may be kneaded, made into pellets and then molded into film by an extruder equipped with T die to give a composite film for preparing the substrate sheet. However, as will be mentioned later, the resin composition is made into film preferably by means of a calendar molding so that the resulting film having excellent precision in thickness can be prepared in a good productivity and in a low cost.

As described in "Plastics", volume 34, number 8, pages 29–35 (1983), for example, a styrene-ethylene-butylene-styrene block copolymer is a block copolymer having a structure of A-EB-A in which A is a block of glassy or hard non-elastic thermoplastic polymer consisting of ethylene while EB is a block of an elastic polymer consisting of ethylene and butylene. Such a block copolymer is sold as Kraton G1650, 1652 and 1657 (all manufactured by Shell Kagaku K. K.) and can be easily available.

As mentioned above, the substrate film in the present invention is a layered film composed of a composite film formed of a resin composition comprising 100 parts by weight of a polyvinyl chloride-polyurethane composite and 2–10 parts by weight of a styrene-ethylene-butylene-styrene copolymer and a polyalkylene terephthalate film adhered with an adhesive to a composite film.

It is preferred that the above-mentioned adhesive is a polyurethane adhesive or, particularly, that of a two-component type which is particularly capable of adhering a polyalkylene terephthalate film with the composite film strongly. Various types of polyurethane adhesive have been known already (e.g., "Handbook of Polyurethane Resins" edited by Keiji Iwata, pages 438–474, published by Nikkan Kogyo Shinbunsha, 1992) and various kinds of products are commercially available as well. In the invention, such commercially available products may be preferably used.

According to the invention, the resin composition comprises 2–10 parts by weight of a styrene- ethylene-butylene-styrene block copolymer per 100 parts by weight of a polyvinyl chloride-polyurethane composite. This is the reason that the resin composition provides a composite film without a problem of undesirable adhesion of film to rolls in the calendar process. Thus, the manufacture of the composite film by a calendar process is made easy according to the invention. In addition, a problem of blocking upon storage of the composite film manufactured by a calendar process in a rolled state as such can be also solved.

Moreover, as mentioned already, since the composite film is composed of a polyvinyl chloride-polyurethane composite and a styrene-ethylene-butylene-styrene block copolymer, a strong adhesion can be achieved between the composite film and the polyethylene terephthalate film. Accordingly, when the transdermal patch of the invention is applied to and then removed from the skin, it is free from such an inconvenience that the adhesive layer is detached from the polyvinyl chloride-polyurethane composite film together with the polyalkylene terephthalate film. That is, there is no problem of the above-mentioned first residual paste where both of them remain on the skin.

According to the invention, it is particularly preferred that 2–8 parts by weight of a styrene-ethylene-butylene-styrene block copolymer are compounded with 100 parts by weight of the polyvinyl chloride-polyurethane composite.

When the amount of the styrene-ethylene-butylene-styrene copolymer in the resin composition is less than 2 parts by weight per 100 parts by weight of polyvinyl chloride-polyurethane composite, it is not possible to afford a strong adhesion between the composite film of the resin composition and the polyalkylene terephthalate film in the preparation of a substrate film by adhesion and layering of those films using a polyurethane adhesive.

On the other hand, when the amount of the styrene-ethylene-butylene-styrene copolymer in the resin composition is more than 10 parts by weight per 100 parts by weight of the polyvinyl chloride-polyurethane composite, the calendar process of the resin composition becomes bad. Thus, the roll lubricity becomes rather strong and the bank does not smoothly rotate whereby the manufacture of the film is disturbed. The precision of the thickness of the resulting film also lowers.

In the manufacture of a substrate sheet by adhesion of the composite film with a polyalkylene terephthalate film using a polyurethane adhesive, it is preferred that a polyurethane adhesive of a two-component type is applied to the polyalkylene terephthalate film, dried, and subjected to a dry lamination to the composite film which has been previously heated.

It is particularly preferred that a polyurethane adhesive of a two-component type containing around 25–50% of solid is applied on a polyalkylene terephthalate film to an extent of 8–16 g/m$^2$ (around 2.0–8.0 g/m$^2$ in terms of the solid), dried to make the thickness of the adhesive after drying around 1.0–8.0 μm or, preferably, around 1.5–5.0 μm and subjected to a dry lamination to a previously heated composite film.

According to the invention, the composite film is composed of a polyvinyl chloride-polyurethane composite and a styrene-ethylene-butylene-styrene copolymer as mentioned above and, therefore, it is possible to give a strong adhesion between the composite film and the alkylene terephthalate film by the use of a polyurethane adhesive. In addition, the substrate sheet and, accordingly, the resulting transdermal patch prepared therefrom are soft and flexible whereby, upon application to skin, the sheet well fits the skin resulting in no feeling of incompatibility.

The resin composition comprising a polyvinyl chloride-polyurethane composite and a styrene-ethylene-butylene-styrene copolymer may contain a high molecular weight plasticizer having an average molecular weight of 1000–10000 so that the resulting film has good texture and fitting to the skin, as well as the resultant substrate sheet neither warps nor curvatures upon application to the skin. However, when the resin composition contains such a plasticizer too much, it bleeds on the film surface. It is necessary that the amount of the plasticizer is within a range of up to 30 parts by weight per 100 parts by weight of the polyvinyl chloride-polyurethane composite As the above-mentioned high molecular weight plasticizer, a polyester plasticizer is particularly preferred. A polyester plasticizer is a viscous and linear polyester having an average molecular weight of about 1000–10000 obtained by a condensation polymerization of a dibasic acid such as adipic acid, azelaic acid, sebacic acid, or phthalic acid, with a glycol such as ethylene glycol, propylene glycol or 1,3-butylene glycol. Preferred specific examples are polypropylene adipate (a polyester consisting of adipic acid and propylene glycol) and polypropylene sebacate (a polyester consisting of sebacic acid and propylene glycol).

However, even in the case of use of a high molecular weight plasticizer, when the substrate sheet composed of a composite film formed of such a resin composition containing the plasticizer and a polyalkylene terephthalate film adhered thereto is stored in a rolled state in an environment of high temperature for a long period (e.g., for three months or longer in summer), before a primer comprising a saturated polyester resin is coated and formed on the surface of the polyalkylene terephthalate film and an adhesive layer comprising a styrene-diene-styrene block copolymer containing a pharmaceutical agent is layered on the primer layer, it now happens that the high molecular weight plasticizer is transferred to the back (i.e., to the surface of the primer layer). Accordingly, even when an adhesive layer comprising a styrene-diene-styrene block copolymer is layered on such a primer layer, it is sometimes impossible to achieve a strong adhesion between the substrate sheet and the adhesive layer.

Therefore, it is preferred even for a high molecular weight plasticizer that the amount thereof to the resin composition is 10 parts by weight at the highest per 100 parts by weight of the polyvinyl chloride-polyurethane composite. However, it is most preferred that, even in the case of a high molecular weight plasticizer, such a plasticizer is not compounded with the resin composition.

It is preferred that the thickness of the composite film formed of a resin composition of a polyvinyl chloride-polyurethane composite and a styrene-ethylene-butylene-styrene copolymer is within a range of 50–150 μm so that no incompatible feeling is recognized when applied to the skin. When it is too thin, the strength is not practically sufficient while, when it is too thick, the sheet is apt to be detached after applying to the skin.

It is further preferred that the composite film contains an appropriate amount of a stabilizer of a so-called non-toxic type. Preferred examples of such stabilizes include calcium-zinc type one which has been well known as a stabilizer for a vinyl chloride resin already although a usable stabilizer is not particularly limited thereto so far as it is of a non-toxic type.

The composite film may further contain inorganic fine particles, particularly fine powder of anhydrous silica or nepheline syenite, having an average particle size range of 3–10 μm as a filler so far as a transparency of the film is not deteriorated. Particularly when such a filler is contained in the composite film, it is now possible to prepare a composite film wherein pulling out (i.e., rewinding in a rewinding step) of the composite film from a roll is easy or, in other words, unrolling ability of the composite film from a roll (i.e., anti-blocking) is excellent even when the ratio of the styrene-ethylene-butylene-styrene copolymer to the polyvinyl chloride-polyurethane composite in the resin composition is made relatively small.

When the ratio of the styrene-ethylene-butylene-styrene copolymer to the polyvinyl chloride-polyurethane composite is made high, there is a tendency that the gelling property of the resin composition at the manufacture of the composite film by a calendar process becomes low but, when the above-mentioned filler is used, such a problem can be avoided.

It is in particular preferred that the refractive index of the filler used is as near as possible to that of the polyvinyl chloride-polyurethane composite so that the resulting transdermal patch becomes translucent. In view of this, it is preferred to use nepheline syenite having a refractive index of 1.53. Such a filler is usually used within a range of 5–30 parts by weight or, preferably, 5–20 parts by weight to 100 parts by weight of the polyvinyl chloride-polyurethane composite.

The composite film may, if necessary, contain appropriate amounts of additives such as pigment, antioxidant, light stabilizer, flame retardant, antistatic agent, ultraviolet absorber, antifungal, or lubricant.

The resin composition may further contain polyvinyl chloride when it is formed into a composite film. However, when the resin composition contains polyvinyl chloride too much, the resulting composite film has bad fitting to the skin. Therefore, the amount of polyvinyl chloride is within a range of up to 30 parts by weight per 100 parts by weight of the polyvinyl chloride-polyurethane composite.

The polyalkylene terephthalate film used in the invention includes a polyethylene terephthalate film or a polybutylene terephthalate film and, preferably, a polyethylene terephthalate film. It is preferred that the polyalkylene terephthalate film has a thickness of not more than 10 μm. When the thickness of the polyalkylene terephthalate film is more than 10 μm, the resulting transdermal patch is hard and its texture and fitting to the skin are significantly bad. A polyethylene terephthalate film having a thickness of 3–5 μm, for example, is used particularly preferably.

It is further preferred that the polyethylene terephthalate film used has a breaking strength (in a longitudinal direction) of within a range of 25–35 kgf/mm$^2$ and a 2%

(longitudinal) modulus (tensile strength) of within a range of 7.5–9.5 kgf/mm$^2$. For example, a polyethylene terephthalate film having, for example, a thickness of 3.5 μm, a breaking strength of 29.4 kgf/mm$^2$ and a 2% modulus of 8.6 kgf/mm$^2$ is used very suitably.

In a preferred embodiment of the invention, the substrate sheet has a back treating layer on a composite film. A primer layer which comprises a saturated polyester resin is formed on a polyalkylene terephthalate film of such a substrate sheet and a styrene-diene-styrene block copolymer containing a pharmaceutical agent is layered and adhered onto the primer layer, thereby providing a transdermal patch according to the invention.

The back treating layer is preferably composed of a coat having a thickness of about 0.5–2 μm comprising a polyurethane resin compounded with fine powder of silica. When its surface is embossed or, preferably, when it is made into the so-called silky embossed surface, surface of the resulting transdermal patch is delustered and is given with a skin-like touch and appearance whereby its feel upon application and design can be improved. The back treating layer is useful also for improving the unrolling ability when the substrate sheet is stored in a rolled state.

Incidentally, the primer layer comprises a saturated polyester resin. This saturated polyester resin can be manufactured by a condensation polymerization of an aromatic dicarboxylic acid (such as terephthalic acid, isophthalic acid or a mixture thereof) or its mixture with an aliphatic dicarboxylic acid (such as adipic acid, sebacic acid or a mixture thereof) with a saturated aliphatic diol (such as ethylene glycol, neopentyl glycol, 1,4-cyclohexanediol or a mixture thereof) by a conventional method.

It is preferred that such a saturated polyester resin has a molecular weight within a range of 15000–20000. Such a saturated polyester resin is commercially available. In the invention, such a commercially available product can be appropriately used.

Such a saturated polyester is dissolved in an appropriate organic solvent (such as toluene) to prepare a primer and that is applied on the surface of a polyalkylene terephthalate film followed by drying to give a primer layer. The thickness of the primer layer is preferably within a range of 1–5 μm. When the thickness of the primer layer is too thin, a desired strong adhesion is not achieved while, when it is too thick, the primer layer is hard and the softness and flexibility which are needed for the resulting transdermal patch are deteriorated. The primer layer is composed of a saturated polyester resin and is inactive to a pharmaceutical agent so that color of the adhesive layer adjacent to the primer layer is not changed.

It is usual in the invention that a composite film and a polyalkylene terephthalate film are adhered by a polyurethane adhesive by means of a dry lamination to prepare a substrate sheet, then a back treating layer is formed on the composite film, and a primer layer is formed on the polyalkylene terephthalate film. However, it is also possible that both back treating layer and primer layer are simultaneously formed on the substrate sheet.

When a primer layer is formed on the substrate sheet and a back treating layer is also formed thereon as such, blocking upon storage of the substrate sheet after winding on a roll can be prevented and the substrate sheet can be easily rewound from the roll upon necessity. When an adhesive layer comprising a styrene-diene-styrene block copolymer containing a pharmaceutical agent is placed on the primer layer of the substrate layer rewound from the roll as such, it is possible to prepare a transdermal patch where the adhesive layer is strongly adhered to the substrate sheet.

The transdermal patch according to the invention has an adhesive layer comprising a styrene-diene-styrene block copolymer containing a pharmaceutical agent of which thickness is usually within a range of 50–200 μm. When the thickness of the adhesive layer is less than 50 μm, adhesion to the skin is weak and is not practical while, when it is more than 200 μm, a cohesive force of the adhesive layer lowers whereupon residual paste on the skin may be resulted upon peeling off from the skin. When it is too thick, the resulting transdermal patch becomes undesirably opaque.

Specific examples of the styrene-diene-styrene block copolymer which constitutes the adhesive layer in the invention are a styrene-butadiene-styrene block copolymer and a styrene-isoprene-styrene block copolymer. Such a styrene-diene-styrene block copolymer may be used as an adhesive either solely or jointly as a mixture thereof. In addition, the adhesive may contain various additives such as plasticizer, tackifier resin, filler or aging preventer, including polyisobutylene, rosin-modified resin, hydrogenated rosin ester, liquid paraffin, and the like.

A styrene-diene-styrene block copolymer has been known already as, for example, described in detail in the above-mentioned JP-A-54-138124. When A is defined as a glassy or hard non-elastic thermoplastic polymer block consisting of styrene and B is defined as an elastic polymer block of conjugated diene such as butadiene or isoprene, the styrene-diene-styrene block copolymer is a block copolymer having a structure of A-B-A in which the block A occupies 10–50% by weight of the total weight of the polymer. Such a styrene-butadiene-styrene block copolymer is commercially available as, for example, Cariflex TR 1101 or TR 1102, while such a styrene-isoprene-styrene block copolymer is commercially available as, for example, Cariflex TR 1107 (all manufactured by Shell Kagaku K. K.).

There is no particular limitation for the method of laminating the adhesive layer containing a pharmaceutical agent on the substrate sheet. For example, an adhesive layer containing a pharmaceutical agent is melted and applied on a substrate sheet. Alternatively, a pharmaceutical agent is dissolved in an appropriate solvent together with an adhesive and applied on a substrate sheet followed by drying.

One specific example is that a primer layer is formed on a substrate sheet while a styrene-diene-styrene block copolymer is compounded, if necessary, with appropriate additives, then heated, melted and cooled, a pharmaceutical agent is added thereto and mixed therewith to homogenize and the mixture is applied on a releasing paper and stuck together with the above-prepared substrate sheet.

There is no particular limitation for the pharmaceutical agent used in the invention so far as it can be absorbed from the skin. Its examples include local stimulant, antiinflammatory agent, analgesic, agent acting to central nervous system (such as hypnotic, sedative, antiepileptic, and agent for psychoneurosis), diuretic, blood pressure depressant, coronary vasodilator, antitussive, expectorant, antiallergic agent, antiarrhythmicagent, cardiovascular agent, sex hormone, adrenocortical hormone, local anesthetic, and antifungal agent. Such pharmaceutical agents may be used either solely or jointly by combining two or more of them.

To be more specific, examples of local stimulant, antiinflammatory agent and analgesic are salicylic acid, methyl salicylate, salicylic acid glycol, L-menthol, peppermint oil, thymol, etc.

Amount of the pharmaceutical agent in the adhesive layer depends upon the type of the agent used and is not particularly limited as well. Usually, however, it is within a range of 1–25% by weight or, preferably, 5–20% by weight.

A polyalkylene terephthalate film has a high affinity for a primer comprising a saturated polyester resin and the primer has a high affinity for an adhesive comprising a styrene-diene-styrene block copolymer containing a pharmaceutical agent as well. Therefore, a strong adhesion is available between the adhesive layer and the polyalkylene terephthalate film and, therefore, also between the adhesive layer and the substrate sheet. Thus, when the product of the invention is applied to and then removed from the skin, the hereinbefore mentioned second residual paste does not occur. In addition, the primer is inactive to the pharmaceutical agent and hence it does not change the color of the adhesive layer.

INDUSTRIAL APPLICABILITY

As described above, the sticky transdermal patch of the invention comprises a composite film formed of a resin composition comprising a polyvinyl chloride-polyurethane composite and a styrene-ethylene-butylene-styrene copolymer, and a polyalkylene terephthalate film adhered using a first adhesive or, preferably, a polyurethane adhesive on one side of the composite film; a primer layer which comprises a saturated polyester resin and is formed on the surface of the polyalkylene terephthalate film and a second adhesive layer comprising a styrene-diene-styrene block copolymer containing a pharmaceutical agent laminated on the primer layer.

Therefore, a polyalkylene terephthalate film and a composite film are strongly adhered by the first adhesive (preferably, by a polyurethane adhesive) whereby, under any environment or under any applying condition, an interlayer detachment does not take place. Especially when it is applied to and then removed from the skin, the hereinbefore mentioned first residual paste, i.e. a phenomenon where the adhesive layer is detached from the composite film together with the polyethylene terephthalate film, does not occur.

In addition, the polyalkylene terephthalate film of the substrate sheet and the adhesive are strongly adhered by a primer comprising the saturated polyester resin. Therefore, there is no hereinbefore mentioned second residual paste when the transdermal patch is applied to and removed from the skin. Moreover, the primer comprises a saturated polyester resin and hence it is inactive to a pharmaceutical agent and does not result in an undesirable color change in the adhesive layer or the primer layer.

Further, in the transdermal patch in accordance with the invention, the resin composition constituting the surface of the substrate sheet is a film which is mainly composed of a polyvinyl chloride-polyurethane composite. Therefore, texture, smoothness and fitting to skin which are all essential as a transdermal patch are excellent. Besides, when a plasticizer is not compounded with the composite film or a compounding amount is reduced, stickiness of the surface due to a bleeding of the plasticizer onto the surface of the composite film does not take place and the feeling on use is excellent.

The transdermal patch in accordance with the invention is translucent and, especially when the back treating layer is made in a form of a delustered polyurethane resin coat by subjecting the surface to a silk-like embossing, the appearance looks like skin and the feeling upon application and the design of the product are excellent.

It should be also noted that when a primer layer is formed on the substrate sheet followed by storing in a rolled state even for a long period, the plasticizer does not bleed to the back (a primer layer). Thus, the adhesive layer can be strongly adhered, as advantageous form the viewpoint of its manufacture.

As a further point, when the resin composition comprising a polyvinyl chloride-polyurethane composite and a styrene-ethylene-butylene-styrene copolymer contains the latter within a predetermined rate, a strong adhesion to the polyalkylene terephthalate film by means of a polyurethane adhesive can be maintained while good calendar processing ability (i.e., a molding ability to film) can be secured as well and, further, even after allowing to stand in a rolled state, no bleeding of the plasticizer to the back (a primer layer) takes place and the adhesive layer can be strongly adhered.

It goes without saying in the present invention that there is a polyalkylene terephthalate film at the side of the adhesive layer containing a pharmaceutical agent and the polyalkylene terephthalate layer functions as an effective barrier layer to diffusion and permeation of the pharmaceutical agent to the composite film. Thus, even when the pharmaceutical agent has a strong diffusing and permeating property, no pharmaceutical agent is diffused and permeated into the composite film. Even when the composite film contains a plasticizer, diffusion and permeation of the plasticizer to the adhesive layer can be inhibited.

EXAMPLES

The present invention will now be further illustrated by way of the following Examples and Comparative Examples although the present invention will never be limited by those examples. As mentioned already, the amount of a pharmaceutical agent in an adhesive layer is usually very small. Therefore, in this specification, an adhesive containing no pharmaceutical agent is melted and applied to a substrate sheet and dried and the adhesive sheet prepared thereby is used in the examples of the invention where the characteristics of the adhesive sheet are used as the substantial characteristics of the transdermal patch.

That is, the adhesion between the composite film and the polyethylene terephthalate film in the substrate sheet is not related to pharmaceutical agents, and, moreover, in the transdermal patch, the effect of a pharmaceutical agent contained in the adhesive sheet has been well known already. Under such circumstances, in the transdermal patch mentioned hereinafter, the adhesive layer comprised of an styrene-diene-styrene block copolymer without pharmaceutical agent was melted and applied onto a substrate sheet to form an adhesive layer, the resulting adhesive sheet manufactured as such was applied to the skin, and the residual paste and the fitting upon detachment were checked. Adhesion between the composite film and the polyethylene terephthalate film in the substrate sheet was measured as well.

Examples 1–5 and Comparative Examples 1 and 2

First, the components as shown in Table 1 were used to prepare a resin composition composed of a polyvinyl chloride-polyurethane composite and a styrene-ethylene-butylene-styrene copolymer, made into a film (composite film) by a calendar process, and the gelling property (roll processing property) of the resin composition in the calendar molding was checked by the following method. The result is shown in Table 1. Then a polyethylene terephthalate film was adhered to the composite film by a dry lamination to prepare a substrate sheet and the adhesion between the layers in the substrate sheet was checked by the following method.

Gelling Property of the Resin Composition (Roll Processing Property)

When a resin composition in which a polyvinyl chloride-polyurethane composite was compounded with a styrene-ethylene-butylene-styrene copolymer was subjected to a roll processing, the case where it was easily and sufficiently gelled was ranked (A), the case where the gelling was partially insufficient although there was no problem in forming a film by a calendar process was ranked (B), and the case where the gelling was insufficient and the film obtained by a calendar process had significant unevenness on the surface and has pinholes as well was ranked (C).

Interlayer Adhesion in the Substrate Sheet:

A polyvinyl chloride-polyurethane composite was compounded with a predetermined amount of a styrene-ethylene-butylene-styrene copolymer and subjected to a calendar molding to give a composite film having a thickness of 70 μm. In the meanwhile, a polyurethane adhesive (of a two-component type) was applied to a polyethylene terephthalate film having a thickness of 50 μm to such an extent that the dry thickness of the adhesive became 2.0 μm, dried by heating at 110° C. for two minutes, and subjected to a dry lamination to the above-prepared composite film followed by aging at ambient temperature for 24 hours.

The resulting layered film was cut in a size of 19 mm×180 mm to give test pieces. A 180° peeling adhesion was measured for the pieces at the tensile rate of 300 mm/minute using an automatic tensile tester of an AGC type. The result was that, when the compounding amounts of the styrene-ethylene-butylene-styrene copolymer to 100 parts by weight of the polyvinyl chloride-polyurethane composite were 0.5 and 10 part(s) by weight, the 180° peeling adhesions were 360, 580 and 730 g/19 mm, respectively.

Then, the compoundings as shown in Table 1 were used and a composite film composed of a polyvinyl chloride-polyurethane composite and a styrene-ethylene-butylene-styrene copolymer having a thickness of 80 μm was manufactured by a calendar method. The film was wound to a roll and the unrolling ability (blocking property) upon rewinding from this roll was checked by the method which will be mentioned later.

Then a polyurethane adhesive (of a two-component type) was applied to a polyethylene terephthalate film having a thickness of 3.5 μm and dried to form a polyurethane adhesive layer having a thickness of 2.0 μm and said layer was subjected to a dry lamination to the previously heated above-mentioned composite film to adhere the polyethylene terephthalate film to the composite film.

Thereafter, a saturated polyester resin (Baylon 20SS manufactured by Toyo Boseki K. K.; containing 20% of solid) was applied to the side of polyethylene terephthalate film of the laminated product of composite film with polyethylene terephthalate film and dried to give a primer layer. Then, an adhesive composed of a styrene-butadiene-styrene block copolymer was melted and applied onto the primer layer to form an adhesive layer whereupon sticky patches of Examples and of Comparative Examples were obtained.

Each of those sticking patches was tested in terms of residual paste (i.e., adhesion of the adhesive with the polyethylene terephthalate film) and of fitting to the skin. The result is given in Table 1. The methods for evaluation of the test items were as follows.

Blocking Property:

When the force for pulling out a composite film having a width of 45 cm at a take up rate of 8 m/minute was less than 1 kg/45 cm and the film was able to be easily pulled out, that was ranked (A); when said force was within a range of 1–3 kg/45 cm and the film was able to be pulled out without substantial problems, it was ranked (B); and when said force was more than 3 kg/45 cm and the film was easily broken upon pulling out, it was ranked (C).

Residual Paste:

An adhesive sheet stamped out in a size of 5 cm ×5 cm was applied on a skin which was previously wiped with alcohol, rubbed by hand for several times and detached, and the residue of the adhesive on the skin was evaluated. "A" stands for that there was no residual paste; "B" stands for that there was partial residual paste and that the residual paste was particularly noted at the edges of the sheet (5% or less); and "C" stands for that 5% or more of the adhesive remained on the skin.

Fitting to the Skin:

A sheet was placed on the back of the hand and its following, close contact, fitting, folding, etc. were judged by naked eye and touch by hand to conduct a total evaluation. "A" stands for that the sheet well followed along the back of the hand and close contact, fitting and adaptability to skin were good; "B" stands for that a bit hard touch was noted although there was no practical problem; and "C" stands for that the sheet was hard and there was no practical value.

TABLE 1

|  | Examples | | | | | Comparative Examples | |
| --- | --- | --- | --- | --- | --- | --- | --- |
|  | 1 | 2 | 3 | 4 | 5 | 1 | 2 |
| Formulation of Composite Film (parts by weight) | | | | | | | |
| Polyvinyl Chloride-Polyurethane Composite | | | | | | | |
| Shore A Hardness: 90 |  |  | 100 |  |  |  |  |
| Shore A Hardness: 80 |  |  |  | 100 |  |  |  |
| Shore A Hardness: 55 | 100 | 100 |  |  | 100 | 100 | 100 |
| SEBS[1] | 2 | 8 | 5 | 5 | 2 | 1 | 15 |
| Stabilizer[2] | 2 | 2 | 2 | 2 | 2 | 2 | 2 |
| Nepheline Syenite[3] |  |  |  |  | 10 |  |  |
| Evaluation | | | | | | | |
| Gelling Property (Roll Processing Ability) | A | B | B | A | A | A | C |
| Blocking Property of Composite Film | B | A | A | A | AA | C | A |
| Interlayer Adhesion of Substrate Sheet (g/19 mm) | 420 | 730 | 510 | 550 | 420 | 390 | 890 |
| Residual Paste | A | A | A | A | A | A | A |
| Fitting to Skin | A | A | A | A | A | A | A |

1) Styrene-Ethylene-Butylene-Styrene Block Copolymer
2) Stabilizer of Calcium-Zinc Type
3) Minex 7 Manufactured by Shiraishi Kogyo K.K. (average particle size: 4.5 μm; refractive index: 1.53

What is claimed is:

1. A transdermal patch which comprises a substrate sheet which comprises a composite film formed of a resin composition consisting essentially of a mixture of 100 parts by weight of a polyvinyl chloride-polyurethane composite and 2–10 parts by weight of a styrene-ethylene-butylene-styrene copolymer, a polyurethane adhesive layer on one side of the composite film, and a polyalkylene terephthalate film adhered to said one side of the composite film by the first polyurethane adhesive layer; a primer layer which comprises a saturated polyester resin and is formed on a surface of the polyalkylene terephthalate film; and a second adhesive layer comprising a styrene-diene-styrene block copolymer containing a pharmaceutical agent layered on the primer layer.

2. The transdermal patch according to claim 1 in which the polyurethane adhesive layer has a thickness of 1.0–7.0 μm.

3. The transdermal patch according to claim 1 in which the polyalkylene terephthalate film is a polyethylene terephthalate film.

4. A substrate sheet for use in a transdermal patch which comprises a composite film formed of a resin composition consisting essentially of a mixture of 100 parts by weight of a polyvinyl chloride-polyurethane composite and 2–10 parts by weight of a styrene-ethylene-butylene-styrene copolymer, a polyurethane adhesive layer on one side of the composite film, and a polyalkylene terephthalate film adhered to the composite film by means of the polyurethane adhesive layer.

5. The substrate sheet according to claim 4 in which the resin composition contains 5–30 parts by weight of inorganic fine particles having an average particle size of 3–10 μm per 100 parts by weight of a polyvinyl chloride-polyurethane composite.

6. The substrate sheet according to claim 5 in which the inorganic fine particles are nepheline syenite.

7. The substrate sheet according to claim 4 in which the polyurethane adhesive layer has a thickness of 1.0–7.0 μm.

8. The substrate sheet according to claim 4 in which the polyalkylene terephthalate film is a polyethylene terephthalate film.

9. The substrate sheet according to claim 4 in which the polyalkylene terephthalate film has on a surface thereof a primer layer comprising a saturated polyester resin.

10. The substrate according to claim 4 in which the composite film has on a surface a back treating layer which comprises a polyurethane resin coat and has an embossed surface.

11. A method for the manufacture of a substrate sheet for use in a transdermal patch which comprises preparing a resin composition consisting essentially of a mixture of 100 parts by weight of a polyvinyl chloride-polyurethane composite and 2–10 parts by weight of a styrene-ethylene-butylene-styrene copolymer, molding the resin composition into a composite film by a calendar process, and then adhering a polyalkylene terephthalate film on one side of the composite film by means of a polyurethane adhesive layer thereby forming the substrate sheet, and forming a primer layer comprising a saturated polyester resin on an outer surface of the polyalkylene terephthalate film.

12. The method according to claim 11 in which the resin composition contains 5–30 parts by weight of inorganic fine particles having an average particle size of 3–10 μm per 100 parts by weight of a polyvinyl chloride-polyurethane composite.

13. The method according to claim 12 in which the inorganic fine particles are nepheline syenite.

14. The method according to claim 11 in which the polyurethane adhesive layer has a thickness of 1.0–7.0 μm.

15. The method according to claim 11 in which the polyalkylene terephthalate film is a polyethylene terephthalate film.

* * * * *